(12) United States Patent
Zhang

(10) Patent No.: US 8,899,094 B1
(45) Date of Patent: Dec. 2, 2014

(54) EVALUATION OF BALLISTIC RESISTANCE OF STEEL IN TERMS OF BALLISTICALLY INDUCED PLASTICITY

(75) Inventor: Xian Jie Zhang, Rockville, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 375 days.

(21) Appl. No.: 13/443,413

(22) Filed: Apr. 10, 2012

(51) Int. Cl.
*G01N 3/28* (2006.01)
*F41H 5/04* (2006.01)

(52) U.S. Cl.
USPC .......................... 73/12.05; 89/36.02; 148/335

(58) Field of Classification Search
None
See application file for complete search history.

(56) References Cited

U.S. PATENT DOCUMENTS

| | | | |
|---|---|---|---|
| 4,634,462 A * | 1/1987 | Fish et al. | 65/29.18 |
| 5,180,450 A | 1/1993 | Rao | |
| 7,981,521 B2 | 7/2011 | Bailey et al. | |
| 8,092,620 B2 | 1/2012 | Sadhukhan et al. | |
| 2010/0143181 A1 | 6/2010 | Sadhukhan et al. | |
| 2012/0144989 A1* | 6/2012 | Du Plessis et al. | 89/36.02 |
| 2012/0174749 A1* | 7/2012 | Stumpf et al. | 89/36.02 |

FOREIGN PATENT DOCUMENTS

JP     EP 1 942 203 A1    7/2008

OTHER PUBLICATIONS

Department of Defense Test Method Standard, V50 Ballistic Test for Armor, Department of Defense, Dec. 18, 1997, 23 total pages.*
Xian Jie Zhang, "Microhardness Characterization in Developing a High-Strength, High-Toughness, and Superior Ballistic Resistance Low-Carbon Ni Steel," presented at the Materials Science & Technology 2011 Conference & Exhibition, Oct. 16-20, 2011, Columbus, Ohio (9 pages).
Dwight Showalter et al., "Development and Ballistic Testing of a New Class of Auto-Tempered High-Hard Steels Under Military Specification MIL-DTL-46100E," Army Research Laboratory, Aberdeen Proving Ground, Maryland, ARL-TR-4997, Sep. 2009.
D. L. McDowell and G. B. Olson, "Concurrent Design of Hierarchical Materials and Structures," Scientific Modeling and Simulation (SMNS), vol. 15, Issues 1-3, pp. 207-240, Apr. 2008.
Latourte et al, "Shear and Tensile Plastic Behavior of Austenitic Steel TRIP-120 Compared with Martensitic Steel HSLA-100," International Journal of Fracture, vol. 162, Nos. 1-2, pp. 187-204, published online Mar. 25, 2010.
Xian Jie Zhang, "Microhardness Characterization in Developing High Strength, High Toughness and Superior Ballistic Resistance Low Carbon Ni Steel," Materials Science and Technology, vol. 28, No. 7, pp. 818-822, Institute of Materials, Minerals and Mining (Jul. 1, 2012).
Xian Jie Zhang, Naval Surface Warfare Center, Carderock Division (NSWCCD), "The Effect of Ballistic-Induced Plasticity (BIP) on the Ballistic Performance of QLT Treated Low-Carbon 10 Ni Steel," Materials Science and Technology Conference (MS&T 2012), Pittsburgh, Pennsylvania, Oct. 7-11, 2012, presented on Oct. 10, 2012.
Dieter Isheim, Allen H. Hunter, Xian Jie Zhang, and David N. Seidman, "Nanoscale Analyses of High-Nickel Concentration Martensitic High-Strength Steels," Metallurgical and Materials Transactions A, The Minerals, Metals & Materials Society and ASM International 2013, vol. 44A, Jul. 2013, pp. 3046-3059.
U.S. Appl. No. 61/888,752, filed Oct. 9, 2013, Inventor Xian Jie Zhang, Title "High-Strength, High-Toughness Steel Compositions and Articles for Ballistic and Cryogenic Applications".

* cited by examiner

*Primary Examiner* — Harshad R Patel
(74) *Attorney, Agent, or Firm* — Howard Kaiser

(57) ABSTRACT

The present invention is typically embodied as a method for studying ballistic resistance of one or more steel materials. A projectile is caused to strike groups of steel samples made of the same steel material, and the ballistic limit $V_{50}$ of each steel material is determined. Prior to the $V_{50}$ testing, a sample of each steel material is metallographically imaged so as to reveal austenitic bodies therein. The austenitic volume fraction of a sample of each steel material is measured via VSM at least once prior to the $V_{50}$ testing and at least once subsequent to the $V_{50}$ testing. Subsequent to the $V_{50}$ testing, a microhardness distribution is mapped characterizing a sample of each steel material in the vicinity of the ballistic crater. The empirical results are assessed in light of the inventively discovered mechanism of plasticity of the steel that is ballistically induced in relation to austenite-to-martensite transformation.

15 Claims, 15 Drawing Sheets

VSM measurements of the volume fraction of austenite

| VSM Sample | Heat Treatment and Deformation History | Volume Fraction of Austenite |
|---|---|---|
| BP76S | Optimally QLT treated and not deformed | 18.98% |
| BP76G | Optimally QLT treated and statically deformed | 9.50% |
| BP76D | Optimally QLT treated and dynamically deformed in ballistic testing | 0.03% |
| BP76N | Fully re-austenitized and quenched into a liquid nitrogen bath | 4.55% |

FIG. 13

Pertinent information about craters BP76-1P and BP05-9

| Crater | Heat treatment | Plate hardness $H_v$ | Initial plate thickness $t_i$, mm | Thinnest cross-section $t_m$, mm | Striking speed %$V_{50B}$ | Global thickness reduction $1 - t_m/t_i$ | Local adiabatic shear band | Failure mode |
|---|---|---|---|---|---|---|---|---|
| BP76-1P | Optimal QLT | 330 | 25.4 | 13.8 | 118 | 46% | No | Bulging |
| BP05-9 | QT | 332 | 22.2 | 16.7 | 89 | 25% | Yes | Plugging |

FIG. 14

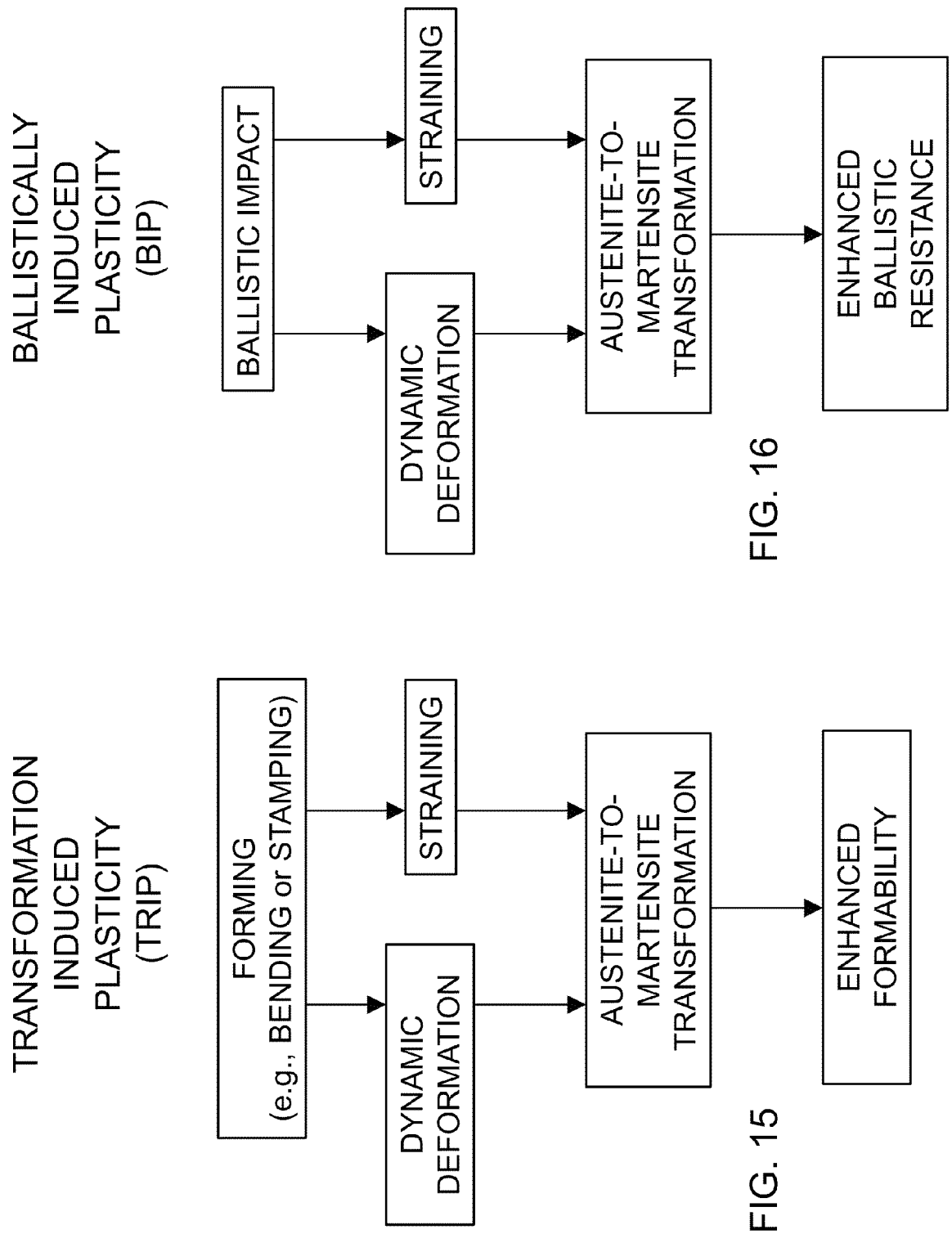

EVALUATION OF BALLISTIC RESISTANCE OF STEEL IN TERMS OF BALLISTICALLY INDUCED PLASTICITY

BACKGROUND OF THE INVENTION

The present invention relates to steel, more particularly to methods for evaluating ballistic properties of steel materials and bodies.

The ballistic perforation of steel targets is a complex process that includes global dynamic deformation, local instable adiabatic shear deformation, strain hardening, phase transformation, and various separation and failure modes. See the following references, each of which is incorporated herein by reference: M. E. Backman and W. Goldsmith: *Int. J. Eng. Sci.*, 1978, 9, 1-99; T. BØrvik, J. R. Leinum, J. K. Solberg, O. S. Hopperstad and M. Langseth: *Int. J. Impact Eng.*, 2001, 25 553-572; Y. B. Xu, J. H. Zhang, Y. L. Bai and M. A. Meyers: *Metall. Trans.* 2008, 39A, 811-843.

Targets behave differently depending on the configuration and characteristics of the target and threat, as well as the ballistic impact velocity and striking angle. See the following references, each of which is incorporated herein by reference: T. BØrvik, J. R. Leinum, J. K. Solberg, O. S. Hopperstad and M. Langseth: *Int. J. Impact Eng.*, 2001, 25 553-572; T. BØrvik, M. Langeth, O. S. Hopperstad and K. A. Malo: *Int. J. of Impact Eng.*, 2002, 27, 19-35; S. Dey, T. BØrvik, O. S. Hopperstad, J. R. Leinum and M. Langseth: *Int. J. Impact Eng.*, 2004, 30, 1005-1038.

Accordingly, there is no universal relationship among microstructure, conventional mechanical properties, and ballistic resistance $V_{50}$. For example, higher hardness enhances the resistance of steel targets to armor piercing (AP) ballistic penetration, but weakens their resistance to fragment simulation projectile (FSP) ballistic perforation. Since microstructure, conventional mechanical properties, and ballistic resistance $V_{50}$ cannot be predictably reconciled, the development of new steels of superior ballistic resistance remains a difficult task.

The following references, each of which is incorporated herein by reference, are informative on ballistic and other properties of steel: T. BØrvik, S. Dey and A. H. Clausen: *Int. J. Impact Eng.*, 2009, 36, 948-964; J. F. Chinella and M. G. H. Wells: ARL-RP-64, US, February 2003; S. N. Dikshit, V. V. Kutumbarao and G. Sundararjan: *Int. J. Impact Eng.*, 1995, 16, 293-320; W. Gooch, M. Burkins and *D. Mackenzie:* 22nd Int. Symposium on Ballistics, Vancouver, Canada, 2005; S. J. Manganello and K. H. Abbott: J. of Materials, 1972, 231-239; D. D. Showalter, W. A. Gooch, M. S. Burkins, J. S. Montgomery and R. Squillacioti: *AMMTIAC,* 2010, Vol. 4, No. 4, 2010; D. D. Showalter, W. A. Gooch, M. S. Burkins and R. Stockman Koch: ARL-TR-4632, US, 2008; D. D. Showalter, W. A. Gooch, M. S. Burkins, V. Thorn, S. Cimpoeru and R. Barnett: ARL-RP-181, US, 2007; D. D. Showalter, W. A. Gooch, M. Burskins, J. Montgomery and R. Squillacioti: ARL-TR-4997, 2009.

SUMMARY OF THE INVENTION

In view of the foregoing, it is an object of the present invention to provide an improved method for evaluating the ballistic resistance of steel.

In accordance with typical practice of the present invention, a method for investigating ballistic resistance of steel includes: (a) measuring the ballistic limit $V_{50}$ of a steel object, the measuring including firing a projectile so that it strikes the steel object and results in a ballistic crater in the steel object; (b) micro-imaging the steel object before the ballistic limit $V_{50}$ is measured so that austenite contained in the steel object is shown in the micro-imaging; (c) measuring the austenitic volume fraction of the steel object at least once before and at least once after the ballistic limit $V_{50}$ is measured; (d) micro-hardness-mapping the steel object after the ballistic limit $V_{50}$ is measured so that the ballistic crater is shown in the micro-hardness-mapping; (e) considering indication by the ballistic limit $V_{50}$ measurement, the micro-imaging, the austenitic volume fraction measurement, and the microhardness-mapping, with respect to existence of a mechanism whereby ballistic resistance of the steel object is enhanced in association with ballistically induced plasticity in the steel object, the ballistically induced plasticity involving transformation of austenite to martensite in the steel object; and, (f) recording information (e.g., paper, computer/electronic, narrative, summary, outline, chronological, numerical, graphical, and/or tabular) pertaining to the considering of the indication with respect to existence of the mechanism.

According to typical embodiments of the inventive method for investigating, each of the following factors may be indicative of the mechanism: a higher measured ballistic resistance $V_{50}$, as opposed to a lower measured ballistic resistance $V_{50}$; based on the micro-imaging, the presence of finer and shorter austenite bodies, as opposed to the presence of coarser and longer austenite bodies; based on the austenitic volume fraction measurements, a greater degree of the transformation of austenite to martensite, as opposed to a lesser degree of the transformation of austenite to martensite in the steel object; based on the austenitic volume fraction measurements, a lower amount of the austenite being left by the transformation of austenite to martensite, as opposed to a higher amount of the austenite being left by the transformation of austenite to martensite; based on the microhardness-mapping, a bulging of the ballistic crater, as opposed to a plugging of the ballistic crater; based on the microhardness-mapping, a greater global thickness reduction of the ballistic crater, as opposed to a lesser global thickness reduction of the ballistic crater; based on the microhardness-mapping, a greater area of a highest-hardness region in the vicinity of the strike location of the ballistic crater, as opposed to a lesser area of a highest-hardness region in the vicinity of the strike location of the ballistic crater; based on the microhardness-mapping, a greater length, along the diameter of the ballistic crater, of a highest-hardness region in the vicinity of the strike location of the ballistic crater, as opposed to a lesser length, along the diameter of the ballistic, crater of a highest-hardness region in the vicinity of the strike location of the ballistic crater.

The present invention features a unique approach to characterizing and considering microhardness and other properties of a steel material in order to evaluate ballistic resistance of the steel material. Inventive measurement and analysis of microstructure, austenite volume reduction via martensite phase transformation, and microhardness can be practiced in order to further the development of a high-strength, high-toughness, and superior-ballistic-resistance steel, such as a low-carbon nickel (Ni) steel.

To develop new steels that exceed the ballistic resistance, strength, and toughness of current naval ship steel plates, the present inventor designed optimally QLT (quench-lamellarize-temper) treated low-carbon 10% Ni steel plates. These plates displayed exceptional properties in all aspects; when compared to the widely-used HSLA-100 steel plates. They showed superior toughness and an improvement of over 15% in strength and 20 mm FSP ballistic limit $V_{50}$.

The present inventor began by conducting extensive chemical composition, processing, structure, mechanical property, and ballistic performance studies on a series of existing and newly designed low-carbon, 2.5-10% Ni steels. An optimally QLT-treated low-carbon 10% Ni—Mo—V steel that substantially outperformed the HSLA100 steel was developed.

The present inventor's preliminary vibrating sample magnetometer (VSM) study on the effect of QLT process, and his dynamic deformation study on microstructure evolution of the 10 Ni steel during ballistic impact, were valuable to his understanding of the steel. The data led the present inventor to conclude that dynamic deformation during ballistic perforation induced an austenite-to-martensite phase transformation, which improves the global dynamic plasticity and ballistic resistance of the steel target.

This mechanism, referred to herein as "ballistically induced plasticity," or "BIP," involves austenite-to-martensite phase transformation as associated with ballistic impact. Ballistically induced plasticity (BIP) is believed to have been first discovered by the present inventor. It was found by the present inventor that characteristics of the microhardness maps of sectioned craters created by ballistics are consistent with "BIP." The present invention's "ballistically induced plasticity" ("BIP") effect is similar to a known mechanism, viz., the "transformation-induced plasticity" ("TRIP") effect.

The present invention's "ballistically induced plasticity" ("BIP") effect is similar to a known mechanism, viz., the "transformation induced plasticity" ("TRIP") effect. TRIP steels are strong and exhibit considerable uniform elongation before failure. During plastic deformation of the TRIP steel, the austenite is transformed into martensite, thus permitting greater elongations and fostering the TRIP steel's attributes of strength and ductility.

Of particular note, the key microstructure—fine and dense austenite precipitates in a strong and ductile ferrite matrix—was identified by the present inventor as the cause of the improvement in ballistic resistance. Inventive analysis of microhardness maps of sectioned craters of ballistic samples, coupled with VSM austenite volume fraction measurements, resulted in development of the inventive underlying theory of how this optimally QLT-treated low-carbon 10% Ni steel can exhibit superior overall properties.

Incorporated herein by reference is the following paper authored by the present inventor and disclosing some aspects of the present invention: Xian Jie Zhang, "Microhardness Characterization in Developing a High-Strength, High-Toughness, and Superior Ballistic Resistance Low-Carbon Ni Steel," presented at the Materials Science & Technology 2011 Conference & Exhibition, 16-20 Oct. 2011, Columbus, Ohio (10 pages).

BRIEF DESCRIPTION OF THE DRAWINGS

The present invention will now be described, by way of example, with reference to the accompanying drawings, wherein:

FIGS. 1 through 4 illustrate superiority, to the other steels, of the optimally QLT treated 10 Ni steel.

FIG. 13 is a table containing VSM measurements of the volume fraction of austenite.

FIG. 14 is a table containing pertinent information about craters BP76-1P and BP05-9.

FIG. 15 is a diagram illustrating transformation-induced plasticity (TRIP).

FIG. 16 is a diagram similar to FIG. 15 and illustrating ballistically induced plasticity (BIP) in accordance with the present invention.

Figure 1:
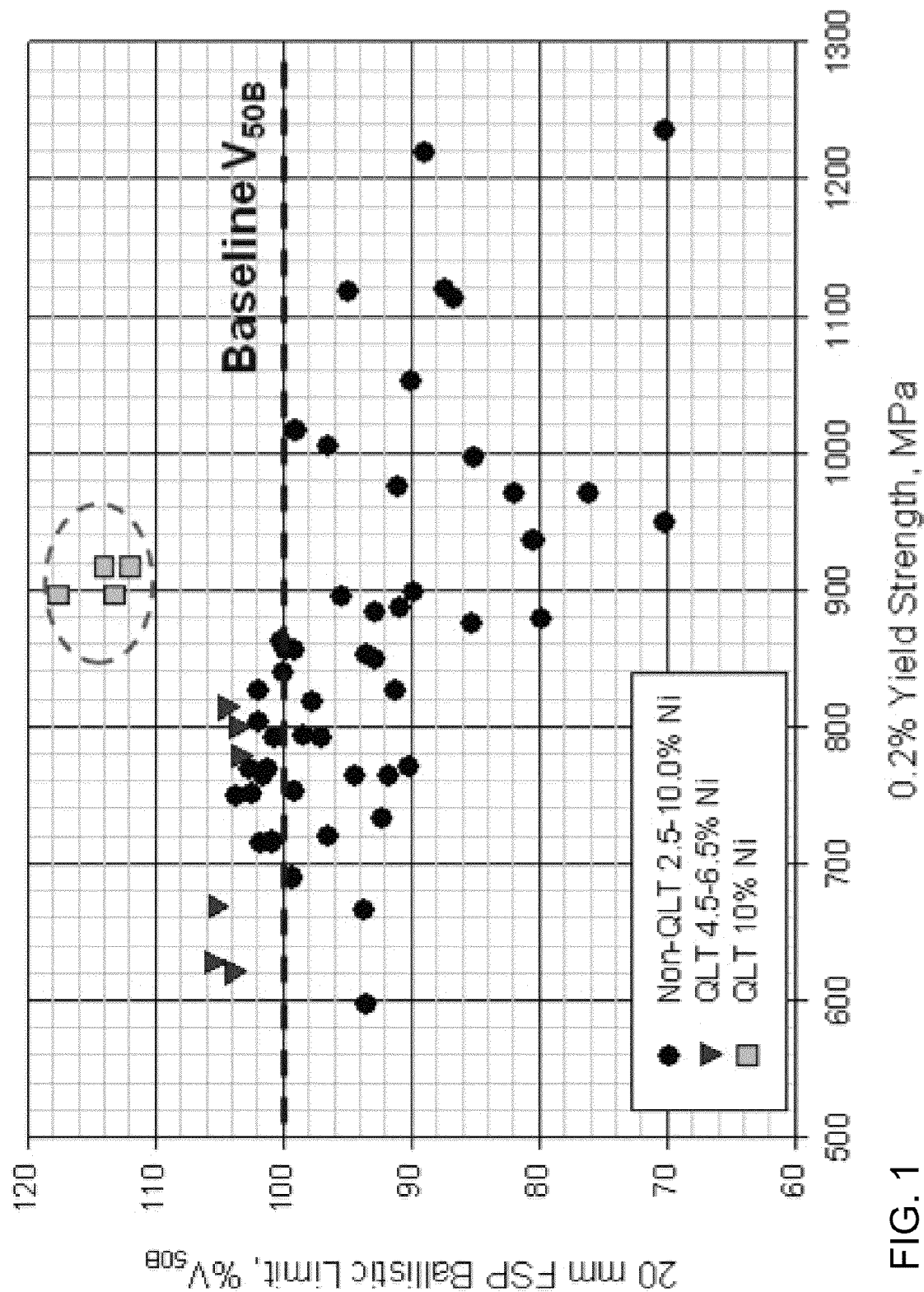
FIGS. 1 through 4 are graphs comparing performances among various steels with respect to various mechanical properties. Each plot displays 20 mm FSP ballistic limit $V_{50}$ (y-axis) versus a mechanical property (x-axis), and compares performances, with respect to a particular mechanical property, among an optimally QLT treated 10 Ni steel and various other steels.
Figure 2:
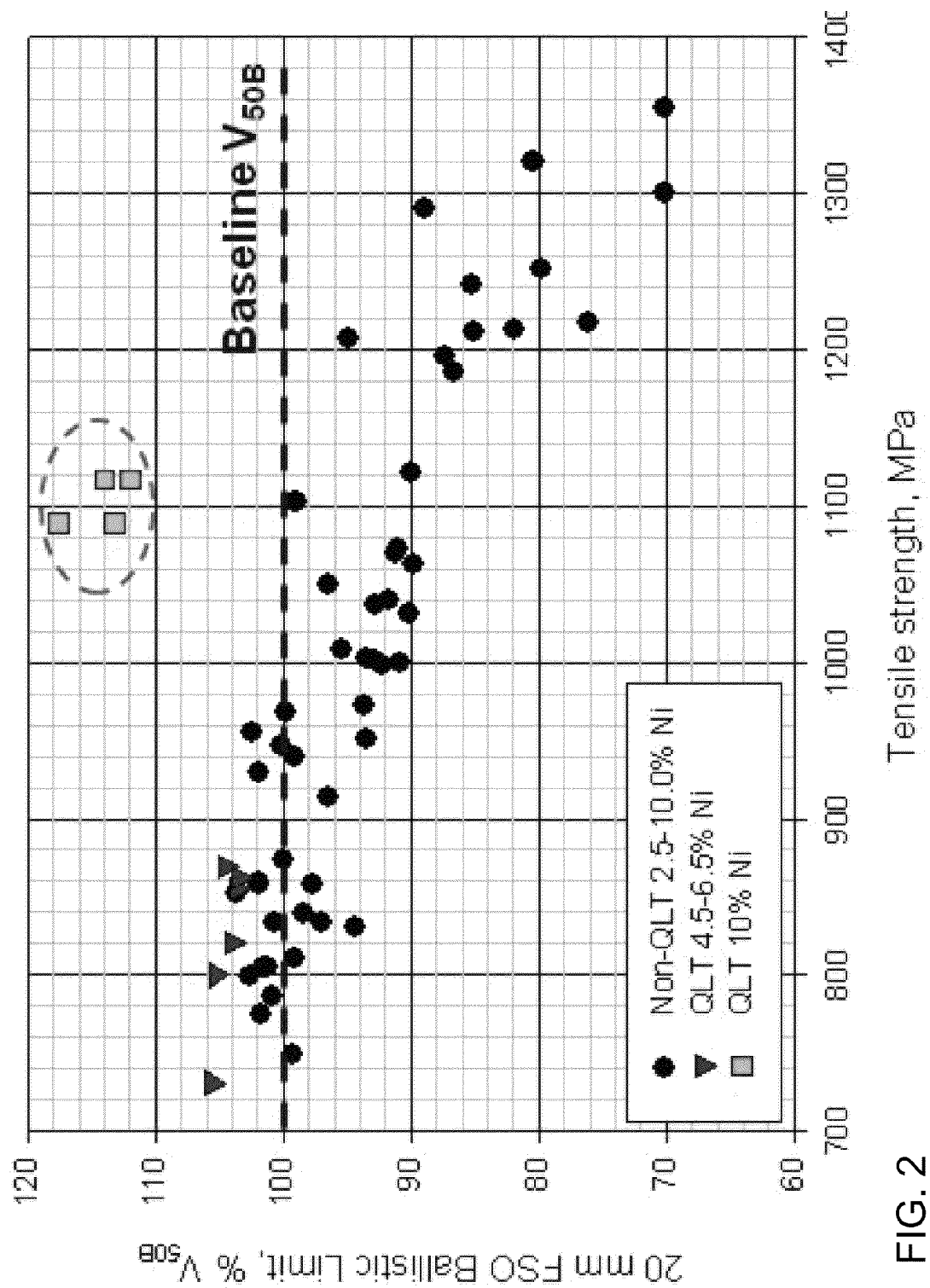
Figure 3:
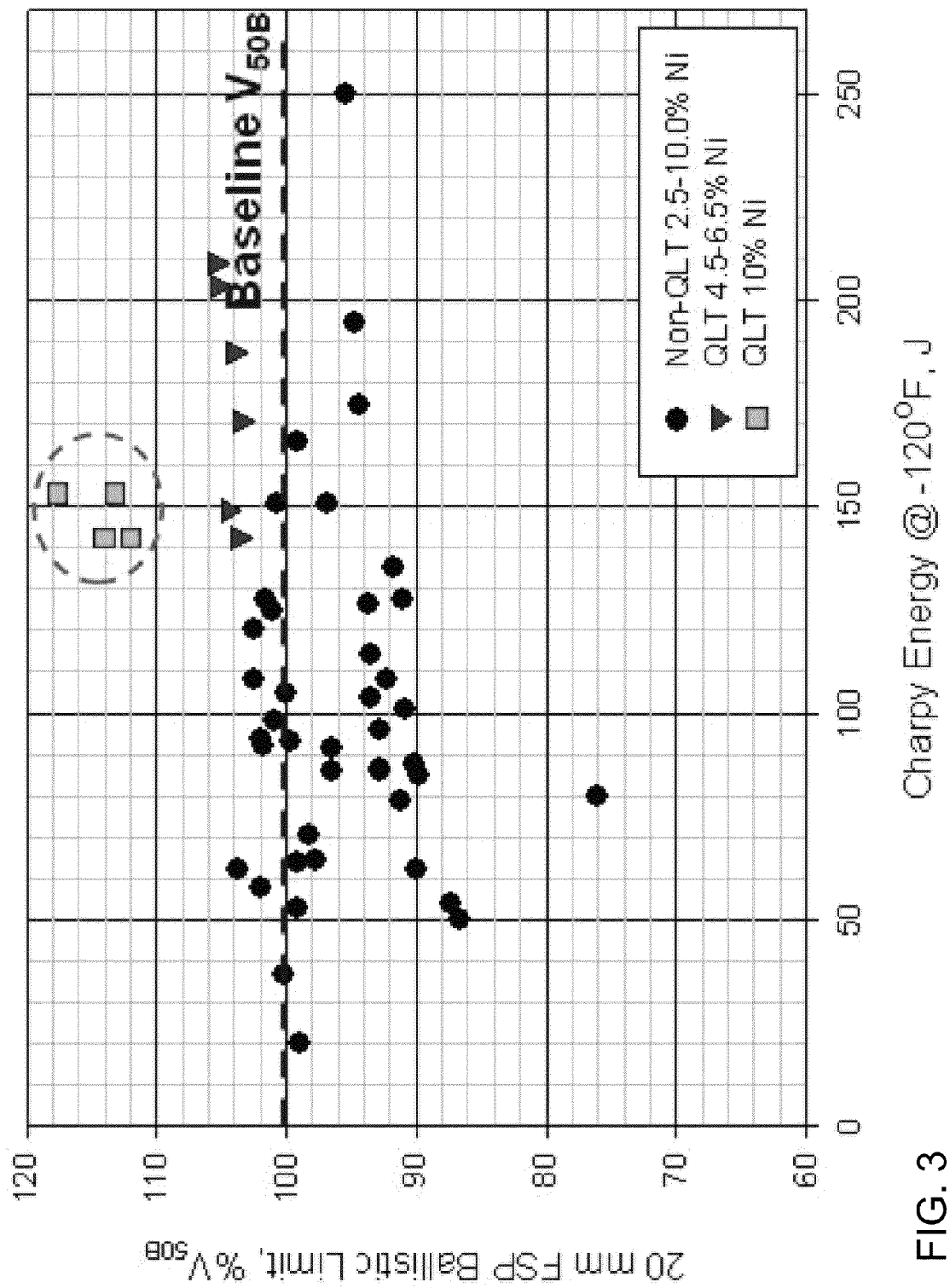
Figure 4:
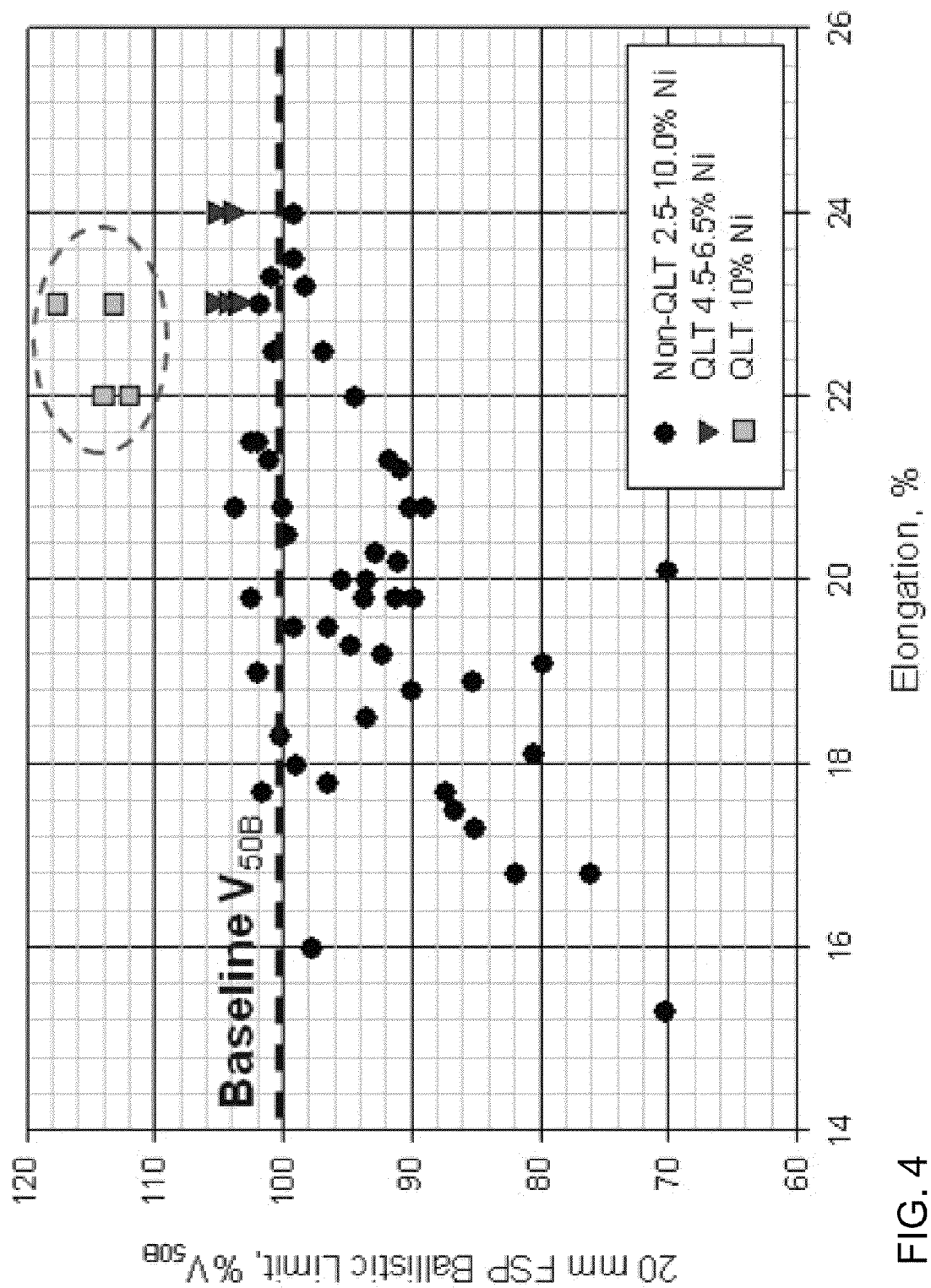

DESCRIPTION OF EXEMPLARY
EMBODIMENTS OF THE INVENTION

Materials and QLT Process

Four optimally QLT treated ballistic test plates of the low-carbon 10% Ni steel were cut from 200 kg vacuum induction melted (VIM) laboratory heats with a nominal composition of 0.10% C, 10% Ni, 1.0% Mo, 0.08% V, 0.60% Mn, 0.60% Cr, and other trace elements. See X. J. Zhang, E. M. Focht and E. J. Czyryca: NSWCCD-61-TR-2006/09, US, 2006, incorporated herein by reference. The ingot dimensions were approximately 20 cm×20 cm×64 cm. The ingot was homogenized at 1260° C. for 7 hours in a gas-fired furnace under a flow of protective nitrogen gas. It was then hot rolled into a 25 mm thick and 203 mm wide plate with a finish rolling temperature of 815° C. The hot rolled plate was air cooled to ambient temperature and cut into 305 mm long pieces.

After an extensive QLT process optimization study utilizing metallographic characterization as well as tensile and Charpy impact tests, an optimal process was determined and used to heat-treat the four ballistic testing plates. The Optimal QLT treatment includes a water quenching from 800° C., a first intercritical heating (L-process) at 630-660° C., a water cool, a second intercritical heating (T-process) at 570-600° C., and a final water cool. The low-carbon 2.5-10% Ni steels samples with various compositions used in this study for comparison were heat-treated with either a QT (quench and temper), QL (quench and lamellarize), or sub-optimal QLT process. Some of the samples were designed by Concurrent Technologies Corporation, 100 CTC Drive, Johnstown, Pa., and QuesTek Innovations LLC, 1820 Ridge Avenue, Evanston, Ill. See J. J. Valencia, et al.: NCEMT-TR-05-029, US, 2005, incorporated herein by reference.

Ballistic and Mechanical Test Results

Twenty millimeter (20 mm) fragment simulation projectile (FSP) ballistic tests were conducted on (i) a group of four ballistic test plates of the optimally QLT-treated low-carbon 10% Ni steel, and (ii) a group of more than fifty ballistic plates cut from non-QLT 2.5-10% Ni steels and QLT 4.5-6.5% Ni steels. The nominal dimensions of the ballistic test plates were 25 mm×203 mm×305 mm, and one 20 mm FSP ballistic limit $V_{50}$ was obtained from each test plate. The tests were performed by the U.S. Army Aberdeen Test Center (ATC) in accordance with the following military specifications, each of which is incorporated herein by reference: Military Specification MIL-STD-662F (Department of Defense Test Standard: "V50 Ballistic Test for Armor") US, December 1997; and, Military Specification MIL-DTL-12560J (MR), US, 2009.

The "ballistic limit $V_{50}$" may be defined as the average velocity of an equal number of the highest partial penetration velocities and the lowest complete penetration velocities that occur within a specific velocity spread. "$V_{50}$," (or "V-50," or "V50") symbolizes "velocity-fifty-percent." In the data presented in FIGS. 1 through 4, the measured ballistic limit $V_{50}$ was normalized to the ballistic limit of a baseline HSLA-100 (2.5% Ni) steel sample, and termed the "$V_{50B}$." Tensile properties and low-temperature (−120° F.) impact toughness data were measured either on small pieces cut from the tested ballistic plates, or small coupons heat-treated with the ballistic plates.

The test results are summarized in FIGS. 1 through 4, which graphically convey ballistic limit $V_{50}$ results (y-axis) versus mechanical properties (x-axis). The optimally QLT treated 10% Ni steel outperformed all other plates, displaying a substantially higher ballistic limit $V_{50}$ at a substantially higher strength level, contradicting a commonly observed reverse-correlation between FSP ballistic limit and strength of steel plates 5, 9, 10, 14, 15. These plates displayed exceptional overall properties including an improvement of more than 15% in both 20 mm FSP ballistic limit $V_{50}$ and strength, as well as superior toughness, when compared to the widely used HSLA-100 steel plates.

The Effect of Microstructure on Ballistic Limit

Figure 5:
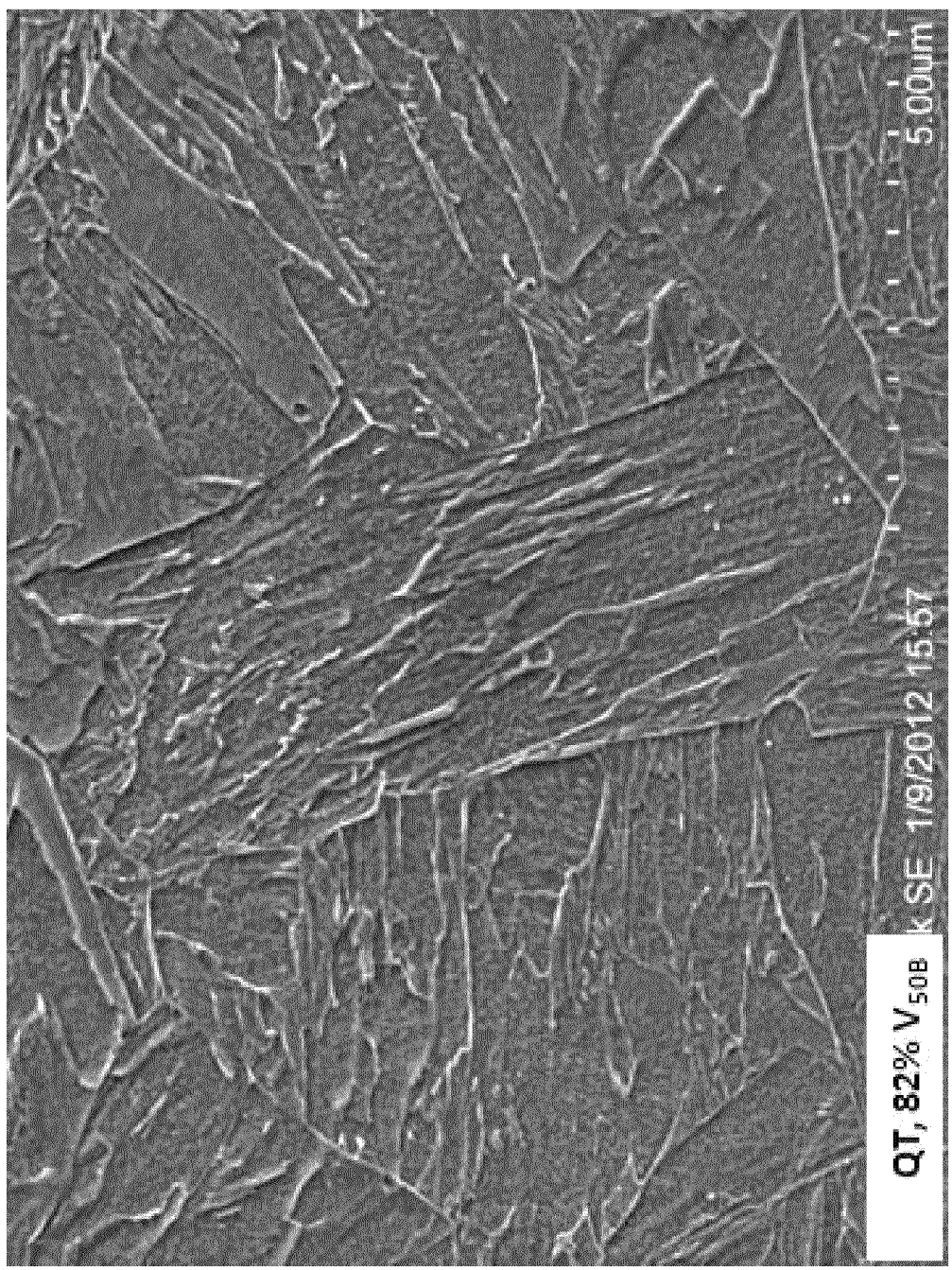
FIG. 5 is a photographic image of a QT treated 10 Ni ballistic sample, tempered lath martensite.
Figure 6:
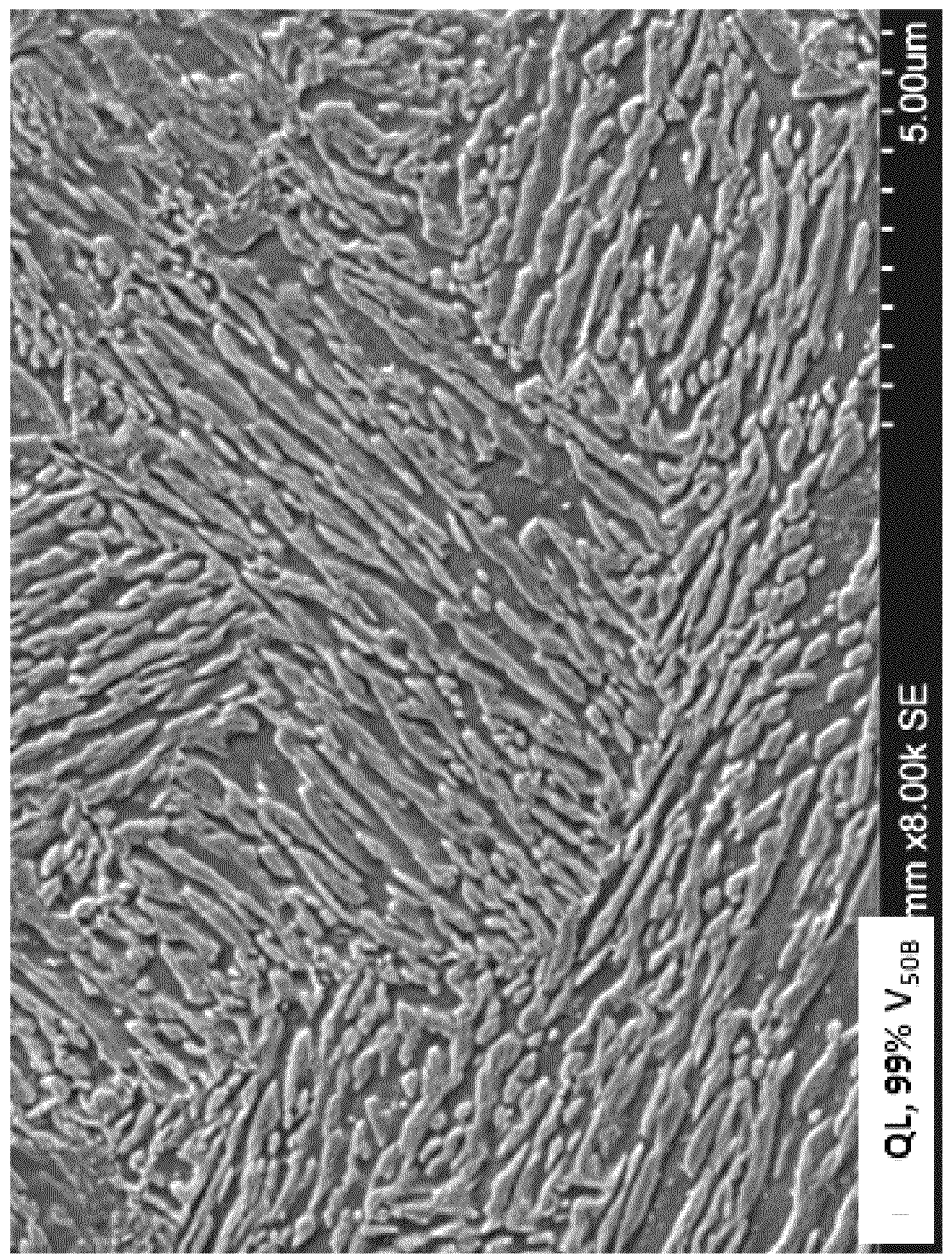
FIG. 6 is a photographic image of a QL treated 10 Ni ballistic sample, long (M+A) rods in a ferrite matrix.
Figure 7:
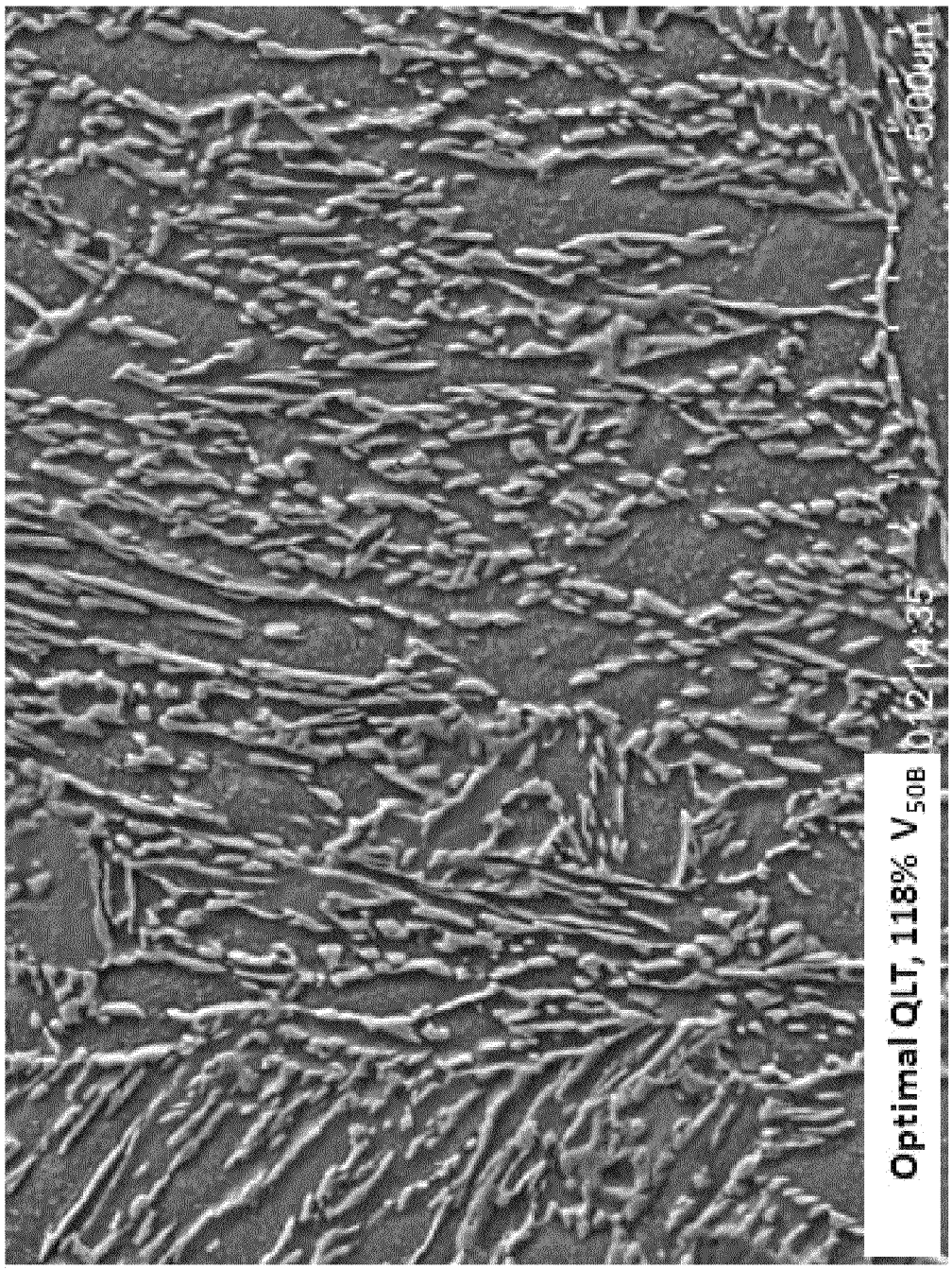
FIG. 7 is a photographic image of an optimal QLT treated 10 Ni ballistic sample, fine austenite precipitates in a ferrite matrix
Figure 8:
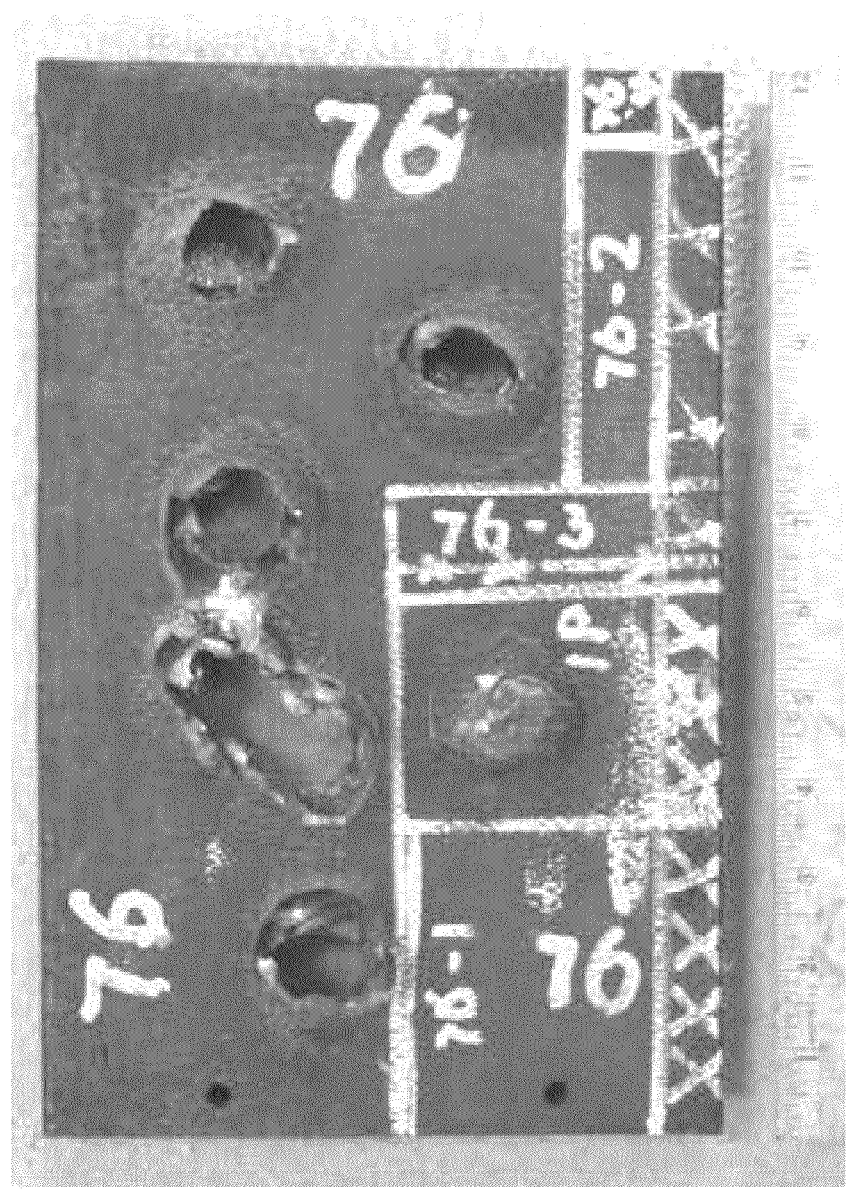
FIG. 8 is a photographic image of an optimally QLT-treated ballistic plate BP76 of low-carbon 10% Ni steel.

From metallographic observations, it was clear to the present inventor that the austenite precipitates were controlling ballistic performance. FIGS. 5 through 7 show microstructures of three low-carbon 10% Ni steel ballistic samples treated with: a QT process, as shown in FIG. 5; a QL process, as shown in FIG. 6; and, an optimal QLT process, as shown in FIG. 7.

Among the three samples, differences were manifest in the amount, size, shape, and distribution of austenite precipitates. These differences correlated with significant differences in ballistic limit $V_{50}$. The QT-treated sample had microstructure consisting of tempered lath martensite (FIG. 5), and exhibited a low 20 mm FSP ballistic limit of 82% $V_{50B}$. The QL sample (FIG. 6) showed long rods consisting of mixtures of martensite and austenite (M+A), which indicated that austenite rods first formed during the intercritical heating (L-process) and then partially transformed to martensite (not revealed in the SEM micrograph) in subsequent cooling, and improving ballistic limit to 99% $V_{50B}$. In the optimally QLT-treated sample (FIG. 7), the long (M+A) rods that formed at the first intercritical heating process (L-process) further decomposed into finer austenite particles and a ferrite matrix in the second intercritical heating process (T-process), resulting in a superior ballistic limit of 118% $V_{50B}$.

These findings by the present inventor are unique insofar as they directly and quantitatively correlate the amount and morphology of a single microconstituent, the austenite precipitates, with the FSP ballistic limit of steel targets. This correlation was also observed by the present inventor among QT, QL, and QLT samples of 4.5% and 6.5% Ni steels. Extensive microstructure evolution analyses using various techniques (OM, SEM, TEM, XRD, EBSD, EDS, EELS, 3D atom-probe, etc.) were performed during this study by the present inventor and his collaborators.

Ballistically Induced Austenite-to-Martensite Transformation as Measured Using a VSM The present inventor perceived that the exceptional performance of the inventive testing's candidate steel warranted further study of the role of (i) microstructure evolution during ballistic impact, and (ii) deformation behavior of each microconstituent in determining the ballistic resistance of the sample.

Prior to performing microhardness measurements and mapping the microhardness measurements, discussed hereinbelow, VSM measurements were performed of volume fractions of austenite. A vibrating sample magnetometer (VSM) was used to measure the austenite volume fraction of several small samples cut from a tested ballistic plate, BP76, which was optimally QLT-treated and displayed a 20 mm FSP ballistic limit of 118% $V_{50B}$.

Figure 9:
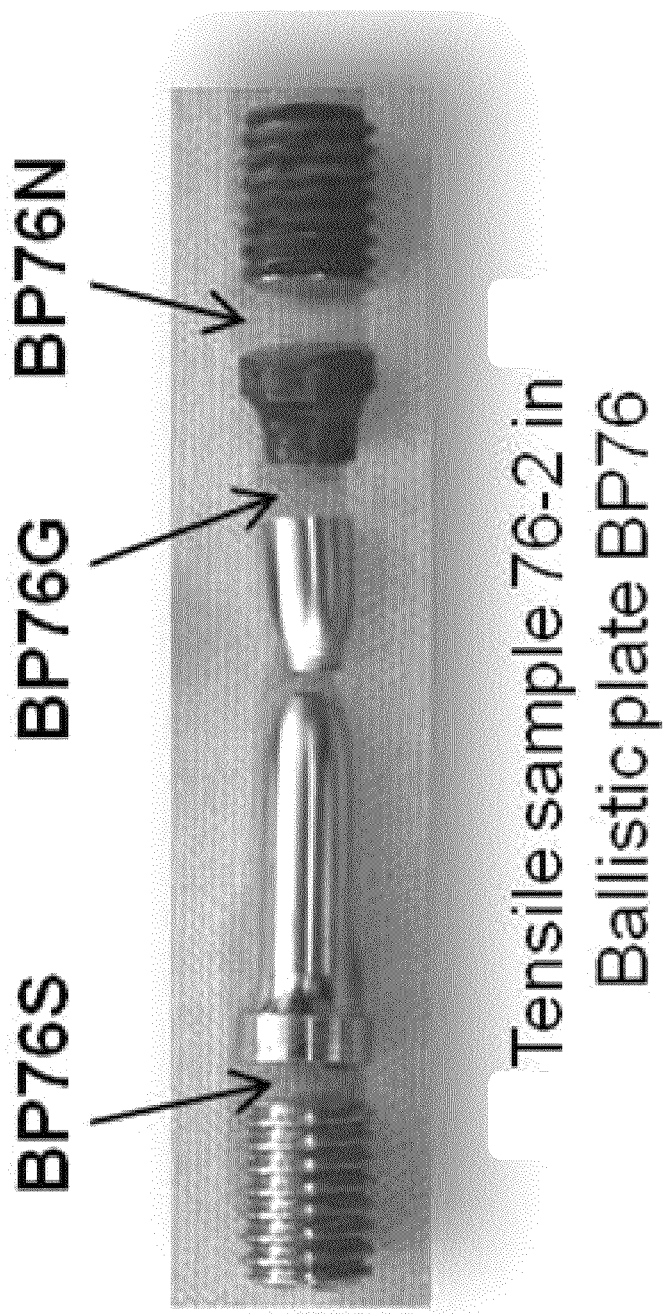
FIGS. 9 and 10 are photographic images showing locations of VSM samples cut from the optimally QLT treated ballistic plate BP76 (of the low-carbon 10% Ni steel) shown in FIG. 8.
Figure 10:
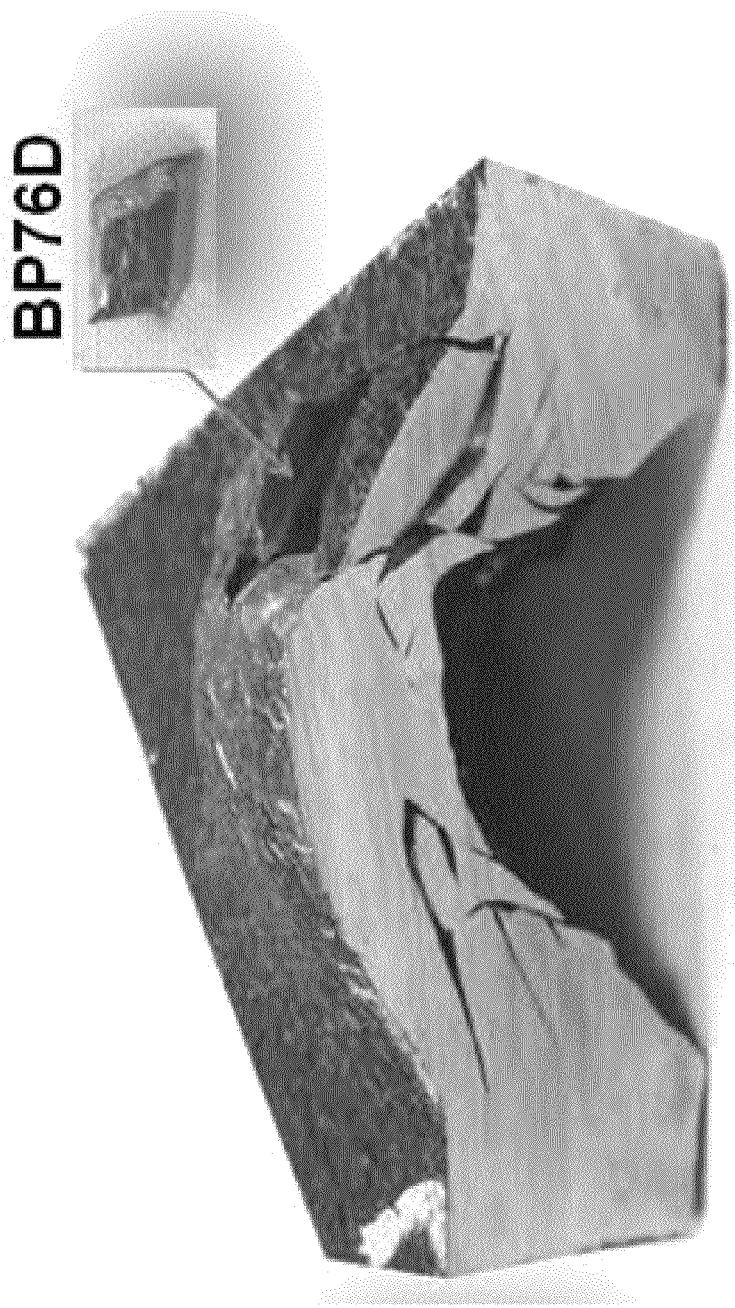

VSM sample BP76S was cut from a shoulder section of a statically tested tensile sample taken from an un-impacted area of the plate, and thus represented the original microstructure formed by the optimal QLT process. For comparison, sample BP76G was cut from the elongated section of the same tensile sample, and therefore was representative of a statically deformed condition. Sample BP76D was removed from a severely deformed area in ballistic crater 1P, representing the condition caused by a projectile striking at the plate's $V_{50}$ speed. Sample BP76N was cut from the other shoulder section of the tensile sample, re-austenitized, and liquid-nitrogen quenched. The locations of these four VSM samples are indicated in FIGS. 9 and 10.

The optimally QLT-treated BP76 contained an initial austenite volume fraction of 19%. The content decreased to 9.5% after deformation in a static tensile test, and was nearly undetectable after the ballistic test (FIG. 13). These changes in austenite volume fraction were informative of the phase transformation and deformation mechanism of the ballistic test piece. The dynamic deformation caused by ballistic impact likely induced an austenite-to-martensite phase transformation that enabled improved ballistic performance of the target plate.

Ballistically Induced Plasticity as Intuitively Revealed by Microhardness Maps

Figure 11:
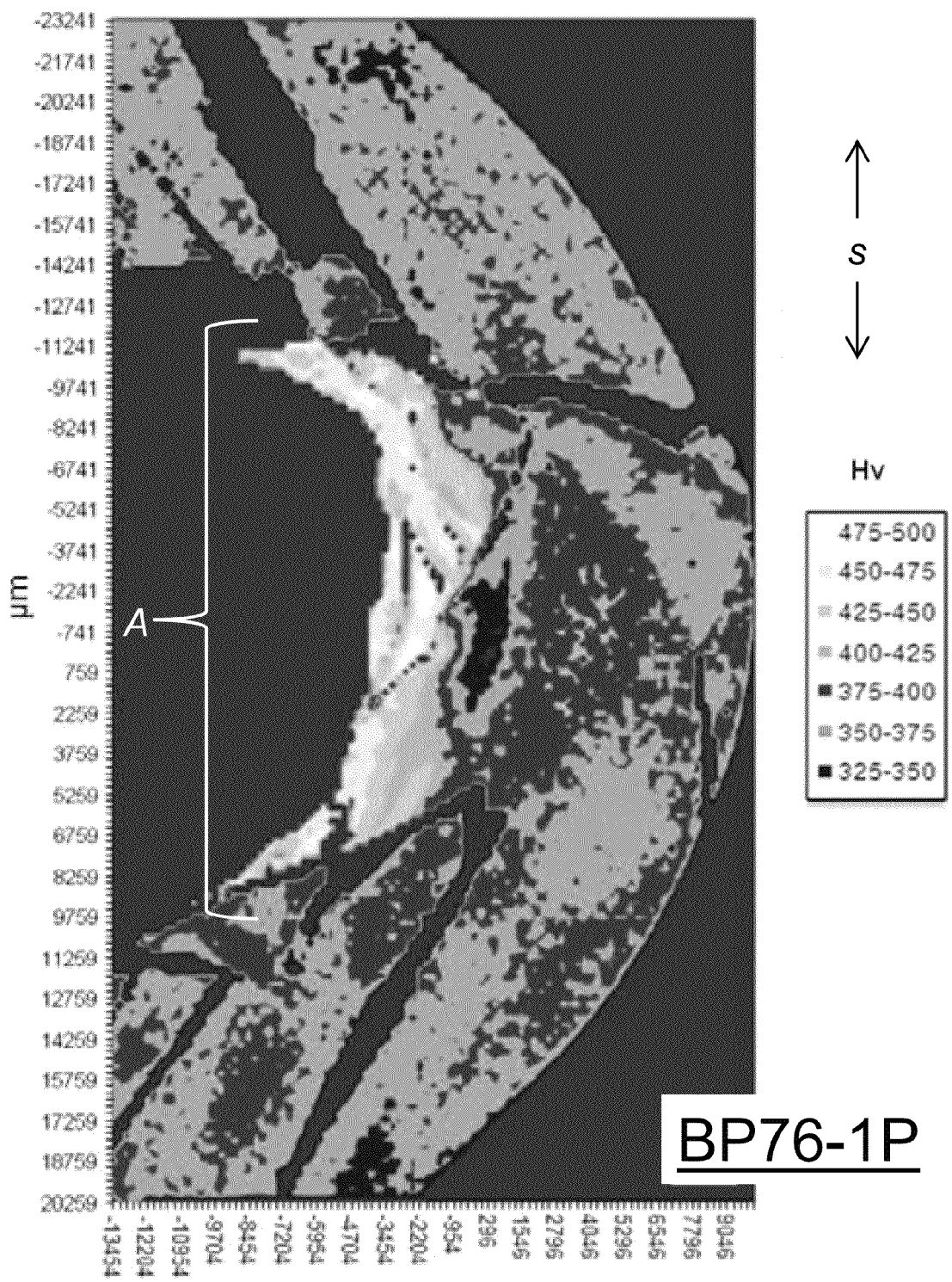
FIG. 11 is a graphically contextualized photographic image conveying a microhardness map of sectioned crater BP76-1P of 10 Ni steel.
Figure 12:
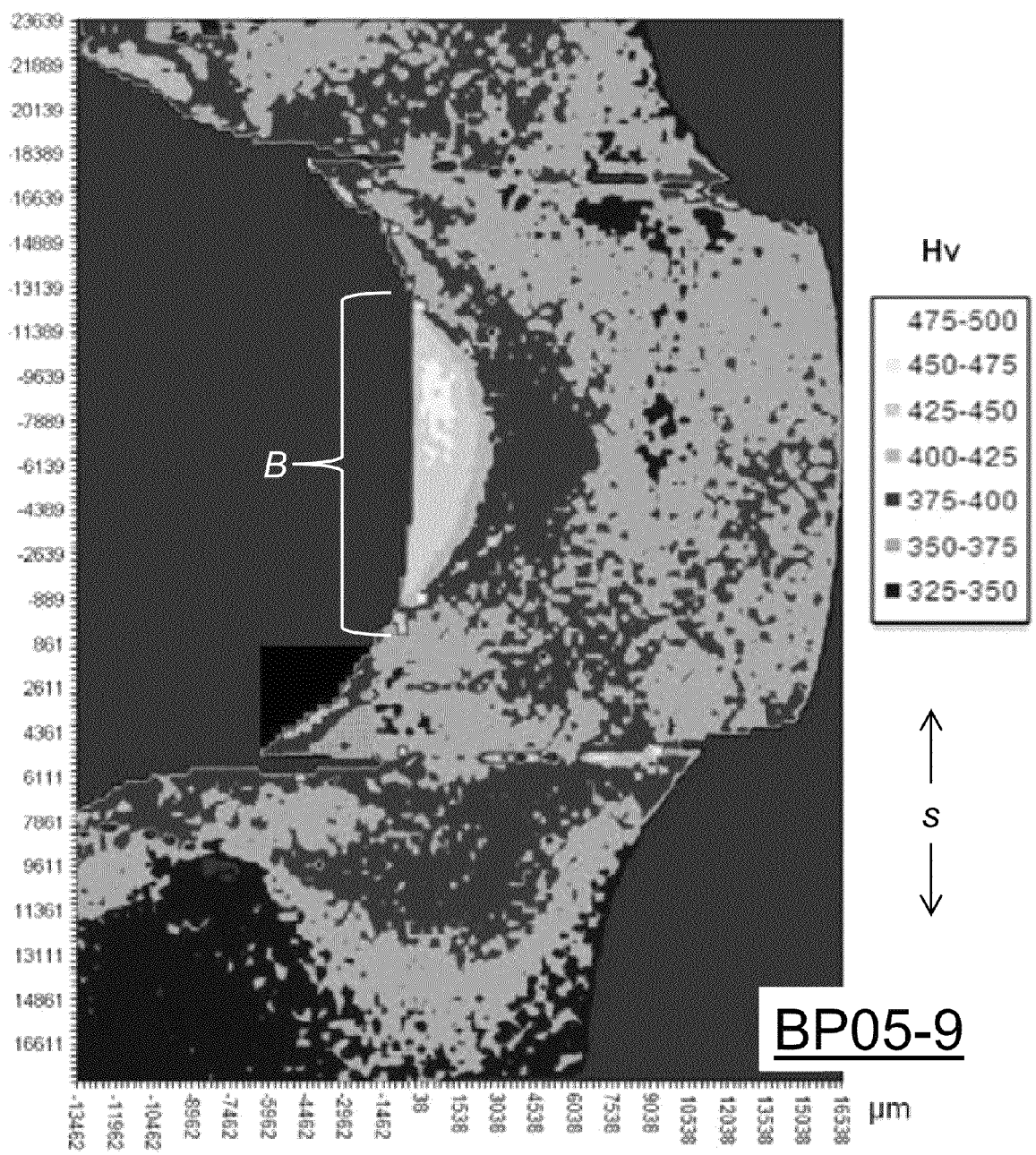
FIG. 12 is a graphically contextualized photographic image conveying a microhardness map of sectioned crater BP05-9 of 10 Ni steel.

These magnetometer results indicated to the present inventor that there must be a critical time window during the microstructure evolution that affects the deformation behavior of targets. With reference to FIGS. 11 and 12, the spatial microhardness distribution of deformed targets was measured by mapping microhardness measurements onto transverse sections of ballistic craters.

FIGS. 11 and 12 are grayscale versions of color microhardness maps obtained by the present inventor. In each figure, seven Vickers hardness (HV) number ranges are shown, viz., 475-500 HV, 450-475 HV, 425-450 HV, 400-425 HV, 375-400 HV, 350-375 HV, and 325-350 HV. The higher a Vickers hardness number, the harder the material. The hardness distribution maps shown in FIGS. 11 and 12 are plotted on the same scale, allowing for intuitive dimensional comparisons. High-hardness region A (shown in FIG. 11) and high-hardness region B (shown in FIG. 12) are the microhardness-map regions that are characterized by the highest hardness ranges, viz., primarily ranging between 425 HV and 500 HV, in their respective microhardness maps.

To map the microhardness measurements, the present inventor used Clemex CMT Lite, a software product manufactured by Clemex Technologies Inc., 800 Guimond, Longueuil, Quebec, J4G 1T5, Canada. One crater from each of two ballistic plates was selected for the mapping. Crater BP76-1P was cut from ballistic plate BP76, which was optimally QLT-treated and exhibited a ballistic limit of 118% $V_{50B}$. Crater BP05-9 was cut from ballistic plates BP05, which were QL-treated with a ballistic limit of 89% $V_{50B}$.

The present inventor found that the 33% higher 20 mm FSP ballistic resistance of BP76 relative to that of BP05 was due solely to differences in their respective heat-treatments (both samples are low-carbon 10% Ni steels with nearly identical chemical composition). The crater for each plate was created by a projectile at its respective $V_{50}$ speed, meaning the striking speed of the projectile for crater BP76-1P was 33% higher than that of crater BP05-9. Microhardness measurements were made 250 μm apart with a load of 300 gf. Results were binned in 25 Hv increments indicated in the key shown in each of FIG. 11 and FIG. 12.

Notable visual comparisons can be drawn between high-hardness region A and high-hardness region B, as revealed in the cross-sectional images of FIGS. 11 and 12. High-hardness region A generally describes an arcuate shape. High-hardness region B generally describes a circular segment shape. High-hardness region A has a greater geometric two-dimensional area than has high-hardness region B. Similarly shown in FIGS. 11 and 12, the plate's ballistic crater generally extends diametrically in transverse direction s, which is approximately perpendicular to the ballistic direction of the projectile. High-hardness region A is more extensive (e.g., longer) than high-hardness region B in transverse direction s. High-hardness region A extends further than high-hardness region B, in transverse direction s, both above and below the immediate strike (impact) area.

FIG. 14 summarizes pertinent information about these two craters before and after ballistic testing. It should be noted that these two plates had identical initial hardness. Important ballistic perforation characteristics of craters BP76-1P and BP05-9 were observed and are discussed hereinbelow.

Using the global thickness reduction, 1—tm/ti, as a simple indicator of the total amount of global dynamic deformation, crater BP76-1P underwent significantly more global deformation than crater BP05-9. In other words, crater BP76-1P absorbed far more kinetic energy of the striking projectile via global deformation than crater BP05-9.

Each hardness distribution map (FIG. 11 and FIG. 12) directly reflects the degree of strengthening and its spread in the crater. The strengthening can occur through either martensite phase transformation strengthening or dynamic strain hardening. Both mechanisms occur during the ballistic perforation process of a crater with substantial austenite content. As the two hardness distribution maps clearly indicate, the strengthening was significantly greater and spread over a larger area in crater BP76-1P (FIG. 11) than in crater BP05-9 (FIG. 12).

The microhardness map findings were consistent with VSM measurements, which showed that almost all of the austenite precipitates (19% volume fraction) in the QLT treated crater BP76-1P transformed into martensite during the ballistic testing. The martensite transformation enhanced the dynamic plasticity and strengthening effect, thus absorbing more kinetic energy, resulting in higher ballistic limit $V_{50}$ of BP76. In comparison, based on magnetometer measurements of similar samples, the BP05 austenite volume fraction was only 5-8%. This was likely the key reason that the BP05 exhibited lower ballistic limit $V_{50}$.

The hardness map of crater BP09-5 showed local adiabatic shear bands (ASBs) that caused a plugging failure. More importantly, because strengthening surrounding the ASBs was moderate and localized, it is evident that this type of process could not dissipate a substantial amount of energy, and resulted in a lower ballistic resistance for BP05. In comparison, there was no indication of the formation of ASB in crater BP76-1P, and the projectile was stopped by extensive plastic bulging of the strengthened target as it absorbed more energy.

The microhardness maps were also informative of the deformation and failure sequence of the ballistic perforation process. Generally speaking, dynamic global deformation must occur prior to local adiabatic sheer banding (ASB) formation. The more dissipated the target deformation is, the less likely ASB is to occur. If the target deforms and strengthens spontaneously upon a strike, the deformation spreads quickly and widely, absorbing much of the energy of the projectile.

As depicted in FIG. 11, because there was less projectile potential energy remaining to cause ASB, the target bulged instead of forming a plug, resulting in a significantly higher ballistic resistance $V_{50}$. The austenite precipitate content in BP76 was sufficient to allow the ballistic-induced austenite-to-martensite transformation to occur. This phenomenon, ballistically induced plasticity, was the key to the improvement of the ballistic behavior of the optimally QLT-treated low-carbon 10% Ni steel.

Evaluating a Steel's Ballistic Resistance Via Ballistic Testing, Metallography, VSM Measurements, and Microhardness Mapping With reference to FIGS. 15 and 16, the present invention's ballistically induced plasticity (BIP) is analogous to transformation-induced plasticity (TRIP). TRIP steels are strong and exhibit considerable uniform elongation before failure. During plastic deformation of the TRIP steel, the austenite is transformed into martensite, thus permitting greater elongations and fostering the TRIP steel's attributes of strength and ductility in association with forming of the TRIP steel. Similarly, the austentite-to-martensite transformation that occurs during plastic deformation of a BIP steel permits greater elongations and fosters the BIP steel's attributes of strength and ductility in association with ballistic impact of the BIP steel.

Figure 17:
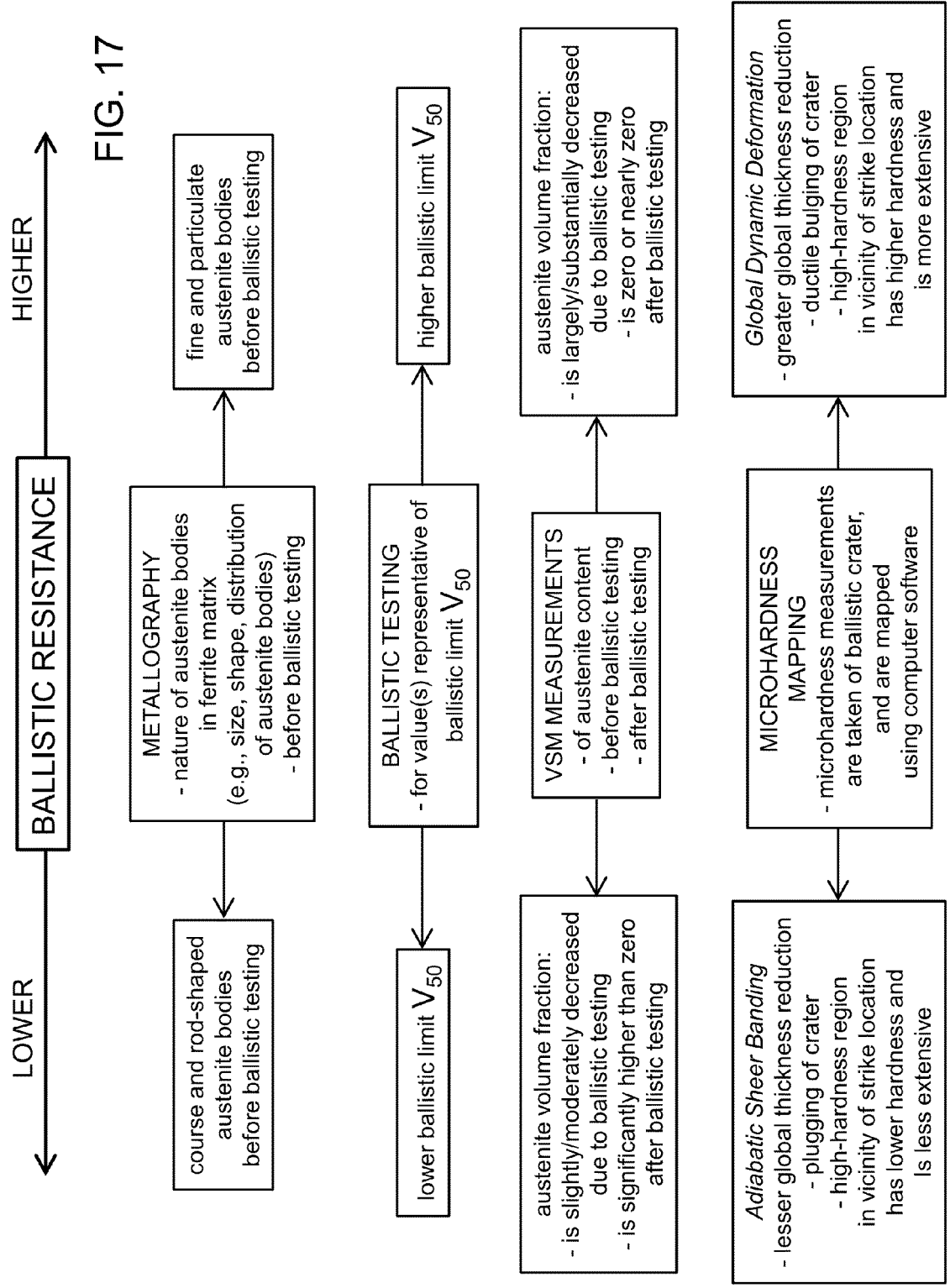
FIG. 17 is a diagram illustrating typical embodiments of ballistic resistance analysis in accordance with the present invention.

Now referring in particular to FIG. 17, the present invention is typically embodied as a method for testing and evaluating ballistic resistance of a steel material.

Ballistic testing of a steel sample is performed. A projectile is caused to strike the steel sample. The steel sample undergoes some degree of austenite-to-martensite transformation during the ballistic testing. At least one value representative of ballistic resistance $V_{50}$ of the steel sample is determined.

Metallography is performed with respect to the steel sample, before the ballistic testing of the steel sample. The metallography includes obtaining at least one metallographic image showing microstructure of the steel sample. Observation of the inventive practitioner of a microstructure characterized by fine and particulate austenite bodies in the steel sample (before the ballistic testing of the steel sample) implies greater ballistic resistance. On the other hand, a microstructure characterized by course and rod-shaped austenite bodies in the steel sample (before the ballistic testing of the steel sample) implies lesser ballistic resistance. The microstructural character of the austenite bodies (e.g., with respect to the number, the sizes, the shapes, and the distribution of the austenite bodies) as shown in the at least one metallographic image is examined.

A first amount and a second amount of austenite in the steel sample are determined, typically using a vibrating sample magnetometer (VSM). The first amount of austenite is determined before the ballistic testing of the steel sample. The second amount of austenite is determined after the ballistic testing of the steel sample. For instance, a volume fraction of the austenite in the steel sample is measured before (e.g., on a non-deformed portion of the steel sample) and again after (e.g., on a ballistically deformed portion of the steel sample) the ballistic testing of the steel sample. The second amount of austentite is less than the first amount of austentite, due to the austenite-to-martensite transformation. According to some inventive embodiments, a third amount of austenite in the steel sample is determined, e.g., by measuring a third volume fraction of the austenite in the steel sample using a VSM on a statically deformed portion of the steel sample before the ballistic testing. A greater decrease in the volume fraction of the austenite in the steel sample, between the first volume fraction and the second volume fraction, implies greater ballistic resistance. A lesser decrease in the volume fraction of the austenite in the steel sample, between the first volume fraction and the second volume fraction, implies lesser ballistic resistance. An approximately zero value of the second volume fraction of the austenite in the steel sample implies greater ballistic resistance.

Microhardness of the steel sample is mapped after the ballistic testing of the steel sample. The microhardness map includes representation of the ballistic crater caused by the ballistic testing. In the microhardness mapping, evidence of global dynamic deformation implies greater ballistic resistance, whereas evidence of adiabatic sheer banding implies lesser ballistic resistance. Global dynamic deformation may be evidenced by the following: greater global thickness reduction of the ballistic crater; ductile bulging of the ballistic crater; higher and more extensive hardness of a high-hardness region in the vicinity of the strike location of the ballistic crater. Adiabatic sheer banding may be evidenced by the following: lesser global thickness reduction of the ballistic crater; plugging of the ballistic crater; lower and less extensive hardness of a high-hardness region in the vicinity of the strike location of the ballistic crater.

The inventive practitioner analyzes (i) the austenite-to-martensite transformation undergone by the steel sample, and (ii) the association between the austenite-to-martensite transformation of the steel sample and ballistic resistance of the steel sample. In conducting his/her analysis, the inventive practitioner considers factors including the following: the microstructural character of the austenite bodies as shown in the metallographic image(s); the determined value(s) representative of ballistic resistance $V_{50}$ of the steel sample; the determined first (pre-ballistic-testing) amount of austenite in the steel sample versus the determined second (post-ballistic-testing) amount of austenite in the steel sample; the hardness distribution as indicated via the microhardness mapping of the steel sample. Usual practice of the inventive method for testing and evaluating a steel material includes recordation of the analysis (including, e.g., results, assessment, and/or conclusions).

The present invention's methodology can be implemented to compare ballistic resistance of two or more steel samples. With respect to each steel sample: ballistic testing is conducted of the steel sample to determine at least one value of ballistic resistance $V_{50}$; previous to the ballistic testing, at least one metallographic microstructure image is obtained of the steel sample that shows austenite in the steel sample; at least once previous to the ballistic testing and at least once subsequent to the ballistic testing, finding the volume fraction of austenite in the steel sample to determine a magnitude of austenite-to-martensite transformation associated with the ballistic testing; subsequent to the ballistic testing, conducting microhardness mapping of the steel sample that shows the nature and extent of crater formation associated with the ballistic testing.

The empirical information thus provided may be evaluated to identify, from among the plural steel samples being tested, at least one steel sample (as constituted prior to ballistic encounter) that is made of a steel material that may be considered to be the most propitious, or among the most propitious, for resisting ballistic impact in one or more contemplated applications. The evaluation of empirical information includes consideration of evidence of ballistic resistance enhancement by virtue of ballistically induced plasticity associated with austenite-to-martensite phase transformation. Data, analysis, conclusions, etc., can be recorded.

According to typical embodiments of the present invention's steel-comparative method, each of the following indications may represent evidence of ballistic resistance enhancement by virtue of ballistically induced plasticity associated with austenite-to-martensite phase transformation: a relatively high ballistic resistance $V_{50}$; the presence in the steel sample, previous to the ballistic testing, of relatively fine and short austenite bodies; a relatively large degree of the austenite-to-martensite transformation associated with the ballistic testing; a relatively small austenite content in the steel sample subsequent to the ballistic testing; a relatively strong characterization of the crater formation as bulging as distinguished from plugging; a relatively large decrease in the global thickness of the crater formation; either or both of a relatively large volume, and a relatively large longitudinal dimension transverse the crater formation, characterizing a maximum-hardness portion at or near the strike surface of the crater formation of the steel sample.

The inventive methodology thus transcends mere ballistic test results as providing the criteria for selection of a particular steel material for a particular purpose. As the present invention is typically practiced, distinctions are drawn between and among metallographic images, VSM-measured austenite content, and computer-aided microhardness mapping so as to attain a deeper understanding of the mechanisms involved in the ballistic resistance, especially insofar as inquiring whether and to what extent the phenomenon of ballistically induced plasticity (BID), discovered by the present inventor, plays a role in the steel-deformative and ballistic-resistive process. For instance, two steel materials may have comparable ballistic limit $V_{50}$ results, but one may be found, through inventive practice, to be more promising because of a more manifest BID influence.

The present inventor's microhardness map analysis, in combination with his VSM measurements and his metallographic imaging, led him to his understanding of the mechanisms underlying the superior overall properties of the optimally QLT-treated low-carbon 10% Ni steel plates. Global dynamic deformation is initiated at the impact area and then spreads forward and laterally. This dynamic deformation instantaneously induces an austenite-to-martensite transformation. These two processes mutually reinforce one another and strengthen the target. However, at a certain point during impact, the local strain and strain rate along the extended lines from the projectile edges may reach a critical combination that can cause the initiation of adiabatic shear band.

The target global deformation and local ASB formation are competing events of the ballistic perforation process. If the former develops quickly and extensively, the latter can be delayed or eliminated. Consequently, the target absorbs a greater amount of kinetic energy of the striking projectile and fails by ductile bulging. This type of steel target displays a higher ballistic limit $V_{50}$, as was observed in the optimally QLT-treated low-carbon 10% Ni steel target BP76 Ballistic-induced martensite phase transformation and dynamic plasticity (BIP) are the key mechanisms behind the remarkable improvement in 20 mm FSP ballistic performance of the optimally QLT-treated low-carbon 10% Ni steel.

The present invention, which is disclosed herein, is not to be limited by the embodiments described or illustrated herein, which are given by way of example and not of limitation. Other embodiments of the present invention will be apparent to those skilled in the art from a consideration of the instant disclosure, or from practice of the present invention. Various omissions, modifications, and changes to the principles disclosed herein may be made by one skilled in the art without departing from the true scope and spirit of the present invention, which is indicated by the following claims.

What is claimed is:

1. A method for investigating ballistic resistance of steel, the method comprising:
    measuring a ballistic limit $V_{50}$ of a steel object, the measuring including firing a projectile so that it strikes the steel object and results in a ballistic crater in the steel object;
    micro-imaging the steel object before the ballistic limit $V_{50}$ is measured so that austenite contained in the steel object is shown in the micro-imaging;
    measuring an austenitic volume fraction of the steel object at least once before and at least once after the ballistic limit $V_{50}$ is measured, a first said austenitic volume fraction measurement being said measuring of the austenitic volume fraction at least once before the ballistic limit $V_{50}$ is measured, a second said austenitic volume fraction measurement being said measuring of the austenitic volume fraction at least once after the ballistic limit $V_{50}$ is measured, the first said austenitic volume fraction measurement being performed using a vibrating sample magnetometer on a non-deformed portion of the steel object, the second said austenitic volume fraction measurement being performed using the vibrating sample magnetometer on a ballistically deformed portion of the steel object;
    microhardness-mapping the steel object after the ballistic limit $V_{50}$ is measured so that the ballistic crater is shown in the microhardness-mapping; and
    considering indication by said ballistic limit $V_{50}$ measurement, said micro-imaging, the first said austenitic volume fraction measurement, the second said austenitic volume fraction measurement, and said microhardness-mapping, with respect to an enhancement of ballistic resistance of the steel object in association with ballistically induced plasticity in the steel object, the ballistically induced plasticity involving transformation of austenite to martensite in the steel object.

2. The method for investigating ballistic resistance of steel as recited in claim 1, further comprising recording information pertaining to said considering of said indication with respect to the enhancement of ballistic resistance of the steel object.

3. The method for investigating ballistic resistance of steel as recited in claim 1, wherein said indication with respect to the enhancement of ballistic resistance of the steel object includes at least one of:
    a higher measured ballistic resistance $V_{50}$, as opposed to a lower measured ballistic resistance $V_{50}$;
    based on the micro-imaging, the presence of finer and shorter austenite bodies, as opposed to the presence of coarser and longer austenite bodies;
    based on the first and second said austenitic volume fraction measurements, a greater degree of the transformation of austenite to martensite, as opposed to a lesser degree of the transformation of austenite to martensite in the steel object;
    based on the first and second said austenitic volume fraction measurements, a lower amount of the austenite being left by the transformation of austenite to martensite, as opposed to a higher amount of the austenite being left by the transformation of austenite to martensite;
    based on the microhardness-mapping, a bulging of the ballistic crater, as opposed to a plugging of the ballistic crater;
    based on the microhardness-mapping, a greater global thickness reduction of the ballistic crater, as opposed to a lesser global thickness reduction of the ballistic crater;
    based on the microhardness-mapping, a greater area of a highest-hardness region in the vicinity of the strike location of the ballistic crater, as opposed to a lesser area of a highest-hardness region in the vicinity of the strike location of the ballistic crater;
    based on the microhardness-mapping, a greater length, along the diameter of the ballistic crater, of a highest-hardness region in the vicinity of the strike location of the ballistic crater, as opposed to a lesser length, along the diameter of the ballistic crater, of a highest-hardness region in the vicinity of the strike location of the ballistic crater.

4. The method for investigating ballistic resistance of steel as recited in claim 3, further comprising recording information pertaining to said considering of said indication with respect to the enhancement of ballistic resistance of the steel object.

5. A method for testing and evaluating ballistic resistance of a steel material, the method comprising:
    performing metallography with respect to a steel sample, said metallography being performed previous to ballistic testing of the steel sample, the performing of the metallography including obtaining at least one metallographic image showing microstructure of the steel sample;
    determining a first amount of austenite in the steel sample, said first amount being determined previous to the ballistic testing of the steel sample, said determining of the first amount of austenite including measuring a first volume fraction of the austenite in the steel sample;
    performing the ballistic testing of the steel sample, said performing of the ballistic testing including causing a projectile to strike the steel sample, and determining at least one value representative of ballistic resistance $V_{50}$ of the steel sample, wherein the steel sample undergoes some degree of austenite-to-martensite transformation during the ballistic testing;
    determining a second amount of austenite in the steel sample, said second amount of austenite being determined subsequent to the ballistic testing of the steel sample, said determining of the second amount of austenite including measuring a second volume fraction of the austenite in the steel sample, wherein the second amount of austentite is less than the first amount of austentite due to the austenite-to-martensite transformation;
    mapping microhardness of the steel sample subsequent to the ballistic testing of the steel sample, the microhardness mapping including the ballistic crater caused by the ballistic testing;

analyzing the austenite-to-martensite transformation undergone by the steel sample, and an association between the austenite-to-martensite transformation of the steel sample and ballistic resistance of the steel sample, wherein said analyzing includes consideration of the following:

a microstructural character of austenite bodies as shown in the at least one metallographic image;

a determined at least one value representative of ballistic resistance $V_{50}$ of the steel sample;

a determined first amount of austenite in the steel sample versus the determined second amount of austenite in the steel sample;

a hardness distribution indicated via the microhardness mapping of the steel sample;

wherein said determining of the first amount of austenite and said determining of the second amount of austenite are each performed using a vibrating sample magnetometer, wherein said measuring of the first volume fraction of the austenite in the steel sample includes using the vibrating sample magnetometer on a non-deformed portion of the steel sample, and wherein said measuring of the second volume fraction of the austenite in the steel sample includes using the vibrating sample magnetometer on a ballistically deformed portion of the steel sample.

6. The method for testing and evaluating ballistic resistance of a steel material as recited in claim 5, further comprising recording information pertaining to said analyzing of the austenite-to-martensite transformation undergone by the steel sample, and of the association between the austenite-to-martensite transformation of the steel sample and the ballistic resistance of the steel sample.

7. The method for testing and evaluating ballistic resistance of a steel material as recited in claim 5, wherein the microstructural character of the austenite bodies includes at least one of a number, plural sizes, plural shapes, and a distribution of the austenite bodies.

8. The method for testing and evaluating ballistic resistance of a steel material as recited in claim 7, wherein:

a microstructure characterized by fine and particulate austenite bodies in the steel sample, previous to the ballistic testing of the steel sample, implies greater ballistic resistance;

a microstructure characterized by course and rod-shaped austenite bodies in the steel sample, previous to the ballistic testing of the steel sample, implies lesser ballistic resistance;

a greater decrease in the volume fraction of the austenite in the steel sample, between the first volume fraction and the second volume fraction, implies greater ballistic resistance;

a lesser decrease in the volume fraction of the austenite in the steel sample, between the first volume fraction and the second volume fraction, implies lesser ballistic resistance;

an approximately zero value of the second volume fraction of the austenite in the steel sample implies greater ballistic resistance;

evidence, in the microhardness mapping, of global dynamic deformation implies greater ballistic resistance;

evidence, in the microhardness mapping, of adiabatic sheer banding implies lesser ballistic resistance.

9. The method for testing and evaluating ballistic resistance of a steel material as recited in claim 8, wherein:

global dynamic deformation is evidenced by the following: greater global thickness reduction of the ballistic crater; ductile bulging of the ballistic crater; higher and more extensive hardness of a high-hardness region in the vicinity of the strike location of the ballistic crater;

adiabatic sheer banding is evidenced by the following: lesser global thickness reduction of the ballistic crater; plugging of the ballistic crater; lower and less extensive hardness of a high-hardness region in the vicinity of the strike location of the ballistic crater.

10. The method for testing and evaluating ballistic resistance of a steel material as recited in claim 9, further comprising recording information pertaining to said analyzing of the austenite-to-martensite transformation undergone by the steel sample, and of the association between the austenite-to-martensite transformation of the steel sample and ballistic resistance of the steel sample.

11. A method for comparing ballistic resistance of plural steel samples, the method comprising:

(a) with respect to each of said plural steel samples, obtaining at least one metallographic microstructure image of the steel sample that shows austenite in the steel sample;

(b) with respect to each of said plural steel samples, conducting ballistic testing of the steel sample to determine at least one value of ballistic resistance $V_{50}$;

(c) with respect to each of said plural steel samples, previous to the ballistic testing and subsequent to the ballistic testing, finding a volume fraction of austenite in the steel sample to determine a magnitude of austenite-to-martensite transformation associated with the ballistic testing, a first said volume fraction of austenite being found previous to the ballistic testing using a vibrating sample magnetometer on a non-deformed portion of the steel sample, a second said volume fraction of austenite being found subsequent to the ballistic testing using the vibrating sample magnetometer on a ballistically deformed portion of the steel sample;

(d) with respect to each of said plural steel samples, subsequent to the ballistic testing, conducting microhardness mapping of the steel sample that shows the nature and extent of a crater formation associated with the ballistic testing;

(e) analyzing information provided by steps (a) through (d) to ascertain at least one steel sample, as constituted previous to the ballistic testing, that is made of a steel material that is the most or among the most propitious for resisting ballistic impact in one or more contemplated applications, said analyzing of information provided by steps (a) through (d) including considering evidence of ballistic resistance enhancement by virtue of ballistically induced plasticity associated with austenite-to-martensite phase transformation.

12. The method for comparing ballistic resistance of plural steel samples as recited in claim 11, further comprising recording information pertaining to said analyzing of information provided by steps (a) through (d).

13. The method for comparing ballistic resistance of plural steel samples as recited in claim 11, wherein at least one of the following is indicative of said ballistic resistance enhancement by virtue of ballistically induced plasticity associated with austenite-to-martensite phase transformation:

a relatively high ballistic resistance $V_{50}$;

the presence in the steel sample, previous to the ballistic testing, of relatively fine and short austenite bodies;

a relatively large degree of the austenite-to-martensite transformation associated with the ballistic testing;

a relatively small austenite content in the steel sample subsequent to the ballistic testing;

a relatively strong characterization of the crater formation as bulging as distinguished from plugging;

a relatively large decrease in the global thickness of the crater formation;

either or both of a relatively large volume, and a relatively large longitudinal dimension transverse the crater formation, characterizing a maximum-hardness portion at or near the strike surface of the crater formation of the steel sample.

14. The method for comparing ballistic resistance of plural steel samples as recited in claim 13, further comprising recording information pertaining to said analyzing of information provided by steps (a) through (d).

15. The method for comparing ballistic resistance of plural steel samples as recited in claim 14, wherein said recording of information pertaining to said analyzing of information provided by steps (a) through (d) includes indicating said at least one steel sample that is made of a steel material that is the most or among the most propitious.

\* \* \* \* \*